United States Patent [19]

Anchors

[11] Patent Number: 5,795,895

[45] Date of Patent: Aug. 18, 1998

[54] COMBINATION ANOREXIANT DRUG THERAPY FOR OBESITY USING PHENTERMINE AND AN SSRI DRUG

[76] Inventor: J. Michael Anchors, 16220 Frederick Rd. Suite 210, Gaithersburg, Md. 20877

[21] Appl. No.: 874,329

[22] Filed: Jun. 13, 1997

[51] Int. Cl.$^6$ .......................... A61K 31/50; A61K 31/135; A61K 31/495

[52] U.S. Cl. .......................... 514/253; 514/640; 514/647; 514/651; 514/654; 514/909

[58] Field of Search .................................. 514/651, 654, 514/647, 640, 253, 909

[56] References Cited

PUBLICATIONS

Medical Letters on Drugs & Therapeutics vol. 36: 107–D, Nov. 1994.

*Primary Examiner*—Leonard Schenkman

[57] ABSTRACT

This is a new therapy and method used to treat moderate and severe exogenous obesity by combining generic phentermine with an SSRI (selective serotonin reuptake inhibitor) drug in specific doses for a brief or even a long duration, 12 months or more. The preferred drugs for the combination are fluoxetine hydrochloride(Prozac), sertraline (Zoloft), fluvoxamine maleate (Luvox) and trazodone hydrochloride (Desyrel).

10 Claims, No Drawings

COMBINATION ANOREXIANT DRUG THERAPY FOR OBESITY USING PHENTERMINE AND AN SSRI DRUG

REFERENCES OF INTEREST

Abenhaim L, Moride Y, Brenot F, et al. Appetite-suppressant drugs and the risk of primary pulmonary hypertension. *N Engl J Med.* 1996;335:609–616.

Anchors M. Fluoxetine Is a Safer Alternative to Fenfluramine in the Medical Treatment of Obesity. *Arch Int Med.* 1997;157:1270.

Anchors M. *Better Than Phen-Fen* PRIMA Publishing, Sacramento Calif. 1997, 250 pages.

Atkinson RC. Combination drug treatment of obesity in a practice setting. *Obes Res.* 1993;1(suppl):204.

Herve P, Launay JM, Scrobohaci ML, et al. Increased plasma serotonin in primary pulmonary hypertension. *Am J Med.* 1995;99:249–254.

Kuczmarski R et al. Increasing prevalence of overweight among U.S. adult: Health and Nutrition Examination Surveys 1960–1991. *J A M A.* 19 94;272:205–212.

Manson J et al. Body weight and mortality among women. *N Engl J Med.* 1995;333:677–685.

Weintraub M. Long-term weight control:the National Heart, Lung, and Blood Institute funded multimodal study. *Clin Pharmacol Ther.* 1992;51:581–585.

BACKGROUND OF THE INVENTION

Various drugs and methods of giving drugs have been used to treat obesity, but all have been inadequate because they are either dangerous, ineffective, or quickly lose their anorexiant effect. The combination of phentermine with a selective serotonin-reuptake ihnibitory (SSRI) drug such as Prozac is both safe and effective as a treatment for exogenous obesity.

Phentermine ($\alpha$-dimethyl-$\beta$-phenylethylamine) has been used as oral monotherapy for obesity since about 1970. Phentermine acts on the cerebral appetite center to reduce appetite. It is effective for about two weeks, but then quickly loses effect. It is not approved by the F.D.A. for use beyond six weeks for this reason. Moreover, phenterrine monotherapy is plagued with frequent side-effects, including nervousness, insomnia and constipation. Because of all these problems, until 1992, less than 500,000 phentermine prescriptions were dispensed in the U.S. each year, even though there were 60,000,000 obese people in the U.S. in need of medical therapy for obesity.

Fenfluramine (N-ethyl-3'-trifluoromethyl-$\beta$-phenyl-$\alpha$-methylethylamine) in its two commercial forms, Pondanuin and Redux, constitutes a second class of anorexiant drug. Fenfluramine is a potent releaser of serotonin from serotonergic neurons impinging on the cerebral appetite center. Serotonin is a natural neurotransmitter involved in brain systems controlling sleep, sex drive and satiety. When combined with phentermine, fenfluramine has the effect of enhancing and extending the anorexiant action of phentermine.

But there is a big problem with fenfluramine. The drug is known to be associated with primary pulmonary hypertension (PPH), a rare, often fatal disorder in which the blood vessels of the lungs are destroyed. The disease is rare in the general population, but fenfluramine was shown in a case control study by Abenhaim et al. to be associated with a thirtyfold increase in PPH.

There is reason to think that fenfluramine causes PPH. Fenfluramine releases stored serotonin from blood platelets. Free serotonin causes constriction of puhnonary blood vessels, resulting in PPH in susceptible individuals. There have already been several reported cases of fatal fenfluramine-associated PPH in the U.S., and the C.D.C. is following a dozen other cases. If Abenhaim's prediction is correct, we can expect to see several hundred deaths from fenfluramine-associated PPH even from the current level of fenfluramine use.

But fenfluramine does not have to be used. Phentermine combined with SSRI drugs, such as Prozac, Zoloft, Luvox or Desyrel, is just as effective as "Phen-fen" in generating weight loss, and the SSRI drugs do not cause PPH. The mentioned drugs are similar in structure to fenfluramine in important respects, but they do not release serotonin directly and they are NOT associated with PPH. In 19,000,000 patients on Prozac, only 8 cases of PPH have been reported, well below the reported frequency in the general population.

In a clinical study by Dr. Anchors, 600 patients were treated with a combination of phentermine and one of the SSRI drugs. Patients in the group lost as much as 130 lbs within a year of treatment; the average weight loss was 18 lbs each. Only 7 patients failed to respond to treatment, and only 8 had to stop the treatment because of minor, reversible side-effects. There were no cases of PPH among study patients.

The combination of phentermine with a selected SSRI significantly reduces all side-effects of the therapy because an appropriate SSRI can be selected to offset the side-effects of phentermine. If a patient suffers constipation from phentermine, Zoloft, a diarrhea-producing drug, can be used to offset the constipation. If phentermine causes insomnia, Desyrel can improve sleep. If phentermine causes loss of sex drive, Luvox can restore it.

Moreover, if the obese patient has co-existing depression, the depression can be treated effectively, along with the weight, by increasing the dose of the SSRI component of the therapy to a dose effective for depression. Fenfluramine is not an antidepressant Diet and exercise advice are helpful, but not necessary adjuncts to the phen-SSRI treatment. The crux of the obesity problem is now known to revolve around excessive appetite, not faulty dietary habits or character defects.

The phen-SSRI combination can be continued as long as necessary to reduce weight to ideal body weight, or near to ideal body weight. Thereafter the therapy can be stopped to see if the weight loss is "locked in". About one-fourth of the patients stay at a constant weight off the medicine after therapy. The other three-fourths gain weight back off the therapy; these patients are then placed on maintenance therapy, consisiting of the lowest dose of phen-SSRI that maintains reduced body weight. Maintenance should be continued as long as necessary to keep the weight in a healthy range, just as any physician would treat hypertension or diabetes life long. No previous medical weight-loss therapy has been recommended for lifelong treatment.

SUMMARY OF INVENTION

This invention embodies combination therapy of generic phentermine together with Prozac, Zoloft, Luvox or Desyrel in the treatment of exogenous obesity. There are few side-effects, no serious side-effects, and the treatment is safer than other currently available, effective medical therapies for obesity. The treatment enables individuals to lose weight effectively, control and eliminate type II diabetes and also treats coexisting depression and/or obsessive-compulsive disorder. The treatment can be given for a long duration, up to life-long if necessary, to reduce weight to ideal body weight and keep it there.

DETAILED DESCRIPTION OF THE INVENTION

The use of phentermine (α-dimethyl-β-phenylethylamine) in the generic form should be taken concurrently with fluoxetine hydrochloride (Prozac) or sertraline (Zoloft) or fluvoxamine maleate (Luvox) or trazodone hydrochloride (Desyrel) to treat exogenous obesity.

The first week the patient is instructed to take 15 mg of generic phentennine by mouth each morning along with 10 mg of fluoxetine or ½ of a 50 mg capsule of sertraline or ½ of a 50 mg capsule of fluvoxamine or 50 mg of trazodone. The SSRI drug can be taken in the morning or at night, whichever is most convenient and comfortable. The phentenmine is taken only in the morning.

After the first week, the patient increases the phentermine dose by taking a full capsule each morning with a little food.

Patients should be instructed to get regular, safe, aerobic exercise. They should generally be instructed to eat a healthy, balanced diet, but no specific instructions regarding portion sizes or calories need to be given. The patient should be advised to eat only when hungry and cease eating when full. Patients should be advised to eat three equal-size meals per day.

Patients should be seen by a physician or other qualified medical practitioner two weeks after the start of therapy and then monthly to check blood pressures, ask about problems and encourage compliance. No specific blood tests, EKGs or x-rays are indicated, in general. However, if weight loss is unusually slow, TSH, cortisol and thyroid panel should be measured. If the patient has preexisting diabetes, the diabetes should be treated to the point that is in moderately good control before the therapy is started to avoid hyperglycemia, but strict control is not necessary.

If the rate of weight-loss is unaccetably slow or a plateau is reached, the phentermine dose may be increased to 45 mg in the morning or to 30 mg bid at breakfast and lunch to achieve the desired rate of weight loss. The SSRI dose never needs to be raised to improve the anorexiant effect, but may be raised to treat coexisting depression.

After the patient reaches ideal body weight or the weight at which the patient is satisfied, the therapy is stopped and the weight is checked a month later. [Patients on 60 mg dose of phentermine should be gradually reduced to 30 mg before the dose is stopped.] If the patient has not gained weight, no flurther medical therapy is needed. If the patient regains weight, the patient should be started on maintenance drug therapy consisting of the lowest doses of phentermine and the selected SSRI that maintain patient's weight at the desired level. Usually this amounts to 15 mg of phentermine and the lowest dose of SSRI once a day or every other day.

Generic phentermine should be used because it is much less expensive and its time course of action best suits the phen-SSRI therapy.

The Indications for phen-SSRI therapy is the treatment of exogenous obesity, when other methods have failed. Patients are candidates for the therapy if their BMI is over 30, or if it is over 25 and they have significant adverse consequences of obesity. The ideal range for obesity, i.e. the definition of normal weight, is a BMI between 19 and 25. BMI is defined as the body weight in kg divided by the square of the height in m.

The Contraindications to the therapy are
diabetes out of control
severe hypertension
angina pectoris
recent myocardial infarction
congestive heart failure
significant tachycardia
epilepsy
hyperthyroidism
severe nervous tics or tremors
schizophrennia
tachycardia
glaucoma
symptomatic gallstones
obstructing enlarged prostate
history of allergies or intolerance to phentenmine or the SSRI drug In addition, patients should not take this therapy while they are taking β-blockers, theophylline, Ritalin or oral β-agonists. Caffeine in the diet should be reduced. SSRI drugs should never be coadministered with fenfluramine because of the possibility of "Serotonin Syndrome".

Phentermine should be stopped two weeks prior to surgery involving general anesthesia to avoid hypotension.

This invention calls for a new use of Prozac and other "anti-depressants" and a new method of treating patients with obesity. The new method is long term and in some cases lifelong and embodies the use of two drugs, that of generic phentermine and Prozac or other suitable SSRI listed here. This is an important new method as it allows for safe, large scale reduction of fat in obese patients, without weight gain. The importance in weight loss for obese patients is that of life and death. There are numerous concomitant risk factors of moderate and morbid obesity. According to the Manson study on women, obese women have four times the risk of dying as a result of cardiovascular disease than those in the general population and twice the risk of dying from cancer than the general population.It has been estimated that there are eight hundred thousand deaths per year in the United States from obesity associated aliments.

The importance of this invention cannot be overstated as the large number of obese people in the United States at high risk is growing each year. Never has a therapy been capable of treating such a large proportion of obese individuals in such a safe and effective manner.

What I claim is:

1. A method of treating obesity its a patient in need of long term treatment which comprises admninistration of an effective amont of an SSRI anti depressant and phenteramine.

2. A method of claim 1 whereas the SSRI anti depressant is selected from the group consistinlg of fluoxetine hydrochloride, setraline, fluvoxamine maleate, and trazodone hydrochloride.

3. The method of claim 2 wherein fluoxetine hydrochloride in an amount of 10 mg and phentermine in an amount of 15 mg is administered daily for the first week followed by the daily administration of 10 mg of fluoxetine hydrochloride and 30 mg of phentermine thereafter until ideal body weight is reached.

4. The method of claim 2 wherein setraline in an amount of 25 mg and phenternmine in an amount of 15 mg is administered daily for the first week followed by the daily administration of 25 mg of setraline and 30 mg of phentermine thereafter until ideal body weight is reached.

5. The method of claim 2 wherein fluvoxamine maleate in an amount of 25 mg and phentermine in an amount of 15 mg is administered daily for the first week followed by the daily administration of 25 mg of fluvoxamine maleate and 30 mg of phentermine thereafter until ideal body weight is reached.

6. The method of claim 2 wherein trazodune hydrochloride in an amount of 50 mg and phentermine in an amount of 15 mg is administered daily for the first week followed by the daily administration of 50 mg of trazodone hydrochloride and 30 mg of phentermine thereafter until body weight is reached.

7. A composition useful in treating obesity which comprises 30 mg of phentermine and 10 mg of fluoxetine hydrochloride.

8. A composition useful in treating obesity which comprises 30 mg of phentermine and 25 mg setraline.

9. A composition useful in treating obesity which comprises 30 mg of phentermine and 50 mg trazodone hydrochloride.

10. A composition useful in treating obesity which comprises 30 mg of phenternine and 25 mg fluvoxamine maleate.

* * * * *